United States Patent [19]

Thigpen

[11] Patent Number: 5,456,805
[45] Date of Patent: Oct. 10, 1995

[54] PURIFICATION PROCESS FOR CYCLIC FORMALS

[75] Inventor: Hubert H. Thigpen, Neuces, Tex.

[73] Assignee: Hoechst Celanese Corporation, Somerville, N.J.

[21] Appl. No.: 185,606

[22] Filed: Jan. 21, 1994

[51] Int. Cl.⁶ .............................. B01D 3/36; C07D 13/02
[52] U.S. Cl. ............................ 203/17; 203/68; 549/430
[58] Field of Search ........................... 203/17, 68, 91; 549/430; 252/DIG. 9

[56] References Cited

U.S. PATENT DOCUMENTS 3,857,759  12/1974  Fiore et al. ............................ 203/29

FOREIGN PATENT DOCUMENTS 0518456  11/1955  Canada ................................. 203/17
0166205   9/1984  Japan .................................. 203/17
1524209   9/1978  United Kingdom ..................... 203/68

OTHER PUBLICATIONS

CA 103(6):39488K.
CA 113(6):4576j.

*Primary Examiner*—Virginia Manoharan
*Attorney, Agent, or Firm*—James M. Hunter, Jr.

[57] ABSTRACT

A purification process for cyclic formals, in which water is efficiently removed from a mixture of a cyclic formal and water which is difficult to be separated from the mixture, thereby obtaining a cyclic formal of high purity which contains only an extremely small amount of water.

The purification process for cyclic formals is characterized by the steps of supplying a mixture of a cyclic formal and water into a distillation tower, effecting distillation while supplying n-pentane into the distillation tower and taking out a purified cyclic formal as a bottom liquid.

5 Claims, 3 Drawing Sheets

PURIFICATION PROCESS FOR CYCLIC FORMALS

BACKGROUND OF THE INVENTION

1. Field of the Invention

The present invention relates to a purification process for cyclic formals which are useful as solvents, intermediates of drugs, starting materials for resins, and the like. More particularly, it relates to an economically advantageous purification process for obtaining cyclic formals of high purity which contains only a very small amount of water, in which water is efficiently removed from a mixture of a cyclic formal and water which is difficult to be separated from the mixture because of the azeotropy between cyclic formal and water.

2. Description of Related Art

Cyclic formals typified by 1,3-dioxolan, 1,4-butanediol formal, diethylene glycol formal, methyl-1,3-dioxolan, etc. are known to be obtainable from cyclizing reactions between a corresponding glycol and an aldehyde, and between a corresponding alkylene oxide and an aldehyde. For example, concerning a method for preparing a typical cyclic formal, 1,3-dioxolan, German patent No. 1914209 discloses a process for preparing it by reacting glycol with formaldehyde in the presence of an acid catalyst, and Ind. Eng. Chem., 46,787 (1954) and U.S. Pat. No. 3,857,759 both disclose a process for preparing 1,3-dioxolan by reacting glycol and paraformaldehyde in the presence of an acid catalyst.

These processes for preparing cyclic formals which employ a glycol and an aldehyde as starting materials involve drawbacks in that the cyclic formal produced and a by-produced water or water which is present in a form of an aqueous aldehyde solution often co-boil (azeotropy), thereby rendering separation of water difficult by ordinary distillation steps.

Taking 1,3-dioxolan as an example, the above mentioned German patent No. 1914209 describes that as much as 7% of water is contained. In order to obtain 1,3-dioxolan of high purity by removing water from a mixture of 1,3-dioxolan and water, the above-mentioned Ind. Eng. Chem., 46,787 (1954) discloses a process in which a reaction distillate containing 1,3-dioxolan and water is added with sodium chloride for phase separation into two phases, and the organic phase is subjected to a purifying distillation for purification, while U.S. Pat. No. 3,857,759 discloses a process in which a reaction distillate is added with cyclohexane before purification. However, the former is not suitable as an industrial purification process, and the latter raises a problem in that water cannot be separated sufficiently for obtaining 1,3-dioxolan of high purity.

These phenomena do not specifically occur only in processes for preparing 1,3-dioxolan, but are common in processes for obtaining cyclic formals which form an azeotropic system with water. Accordingly, an economical purification process for obtaining cyclic formals of high purity by which water is efficiently removed from a mixture of a cyclic formal and water has still been desired.

Under the above circumstances, the present inventors have carried out extensive studies in order to solve the aforementioned problems. Based on the phenomenon that water co-boils together with various solvents, which is called azeotropy between water and solvents, they have carefully studied on physicochemical properties of cyclic formals, water, azeotropes between cyclic formals and water, etc., and, as a result, have found that if n-pentane is added to a distillation system of a crude cyclic formal containing water, it destroys the azeotropic system between the cyclic formal and water to effectively distill off water together with n-pentane, thereby yielding 1,3-dioxolan of high purity as a bottom liquid of the distillation tower, and that this method is excellent in view of operation, leading to completion of the present invention.

SUMMARY OF THE INVENTION

Accordingly, an object of the present invention is to provide a purification process for a cyclic formal which comprises the steps of supplying a mixture of a cyclic formal and water into a distillation tower, effecting distillation while supplying n-pentane into the distillation tower, and taking out a purified cyclic formal as a bottom liquid.

Another object of the invention is to provide a purification process for a cyclic formal as described above, wherein the quantity of the n-pentane supplied is from 5 to 20 times, on a weight basis, the quantity of water in the mixture of cyclic formal and water.

Another object of the invention is to provide a purification process for a cyclic formal as described above, wherein a pre-concentrated mixture which contains a cyclic formal having a concentration more than 80% by weight up to a concentration which forms an azeotrope is supplied to the tower.

Another object of the invention is to provide a purification process for a cyclic formal as described above, wherein the cyclic formal is 1,3-dioxolan.

The above and other objects, features and advantages of the present invention will become apparent from the following description.

DETAILED DESCRIPTION OF THE INVENTION AND PREFERRED EMBODIMENTS

Figure 1:
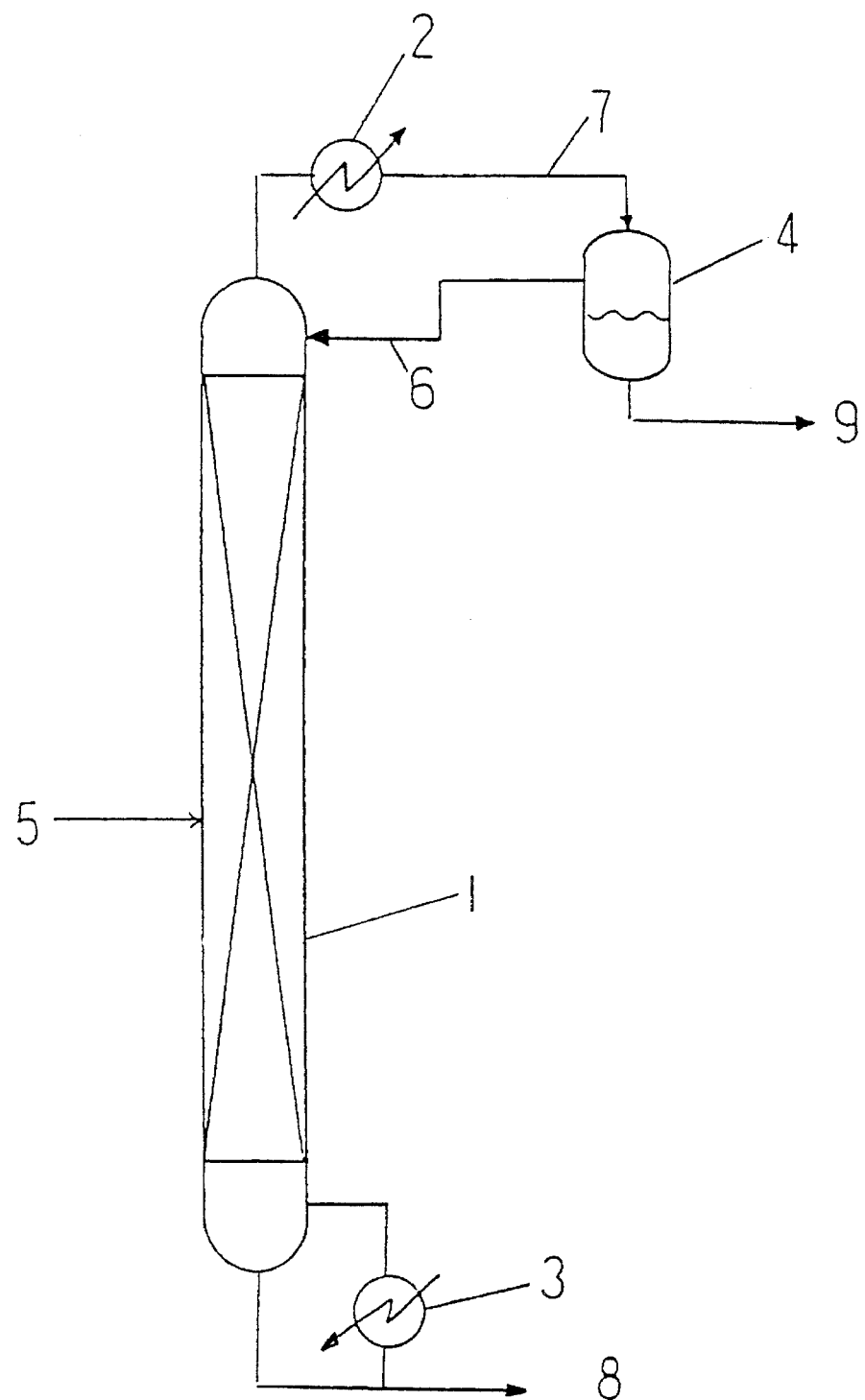
FIG. 1 is a schematic diagram showing a conceptional example of the distillation system used for performing the purification process for cyclic formals according to the present invention.

The present invention will now be described with reference to an example of the distillation system shown in FIG. 1. In FIG. 1, numeral 1 indicates a distillation tower, numeral 2 indicates a condenser, numeral 3 indicates a reboiler, numeral 4 indicates a decanter, numeral 5 indicates a supply position of a mixture containing a cyclic formal and water, numeral 6 indicates a supply position of n-pentane, numeral 7 indicates a distillate at the top (may be referred to as a top distillate), numeral 8 indicates a bottom liquid and numeral 9 indicates a waste of aqueous phase. As described hereinbefore, purification of a cyclic formal involves a limitation, that is, it cannot be purified beyond the azeotropic composition of a cyclic formal and water by ordinary distillation procedures. However, according to the present invention, the presence of n-pentane separately supplied into the distillation tower destroys the azeotropic system between the cyclic formal and water formed in ordinary distillations, allowing water to be removed together with n-pentane, part of the cyclic formal and impurities such as formaldehyde and byproducts of the reaction from the top of the tower. Meanwhile, a very purified cyclic formal from which water and low-boiling point impurities are removed is taken out as a bottom liquid.

The n-pentane useful in the practice of the present invention may be a pure n-pentane or those which primarily contain n-pentane but also contain small amounts of other hydrocarbons. In view of economy, it is advantageous to cool the top distillate containing n-pentane and water for allowing it to separate into two phases of a solvent phase and an aqueous phase, and to re-supply the separated solvent phase which dominantly contains n-pentane into the distillation tower 1 as shown in FIG. 1. This is an economical operation which suffices to achieve the purpose of the present invention, namely purification of cyclic formals.

The amount of n-pentane to supply is not particularly limited. Small amounts of n-pentane invite poor efficiency in the purification of cyclic formals because water would transfer toward the bottom of the tower, while excessive amounts call for high energy for having n-pentane distilled off from the top of the tower, which causes economical disadvantage. Accordingly, the amount of n-pentane to be supplied is generally from 5 to 20 times, particularly preferably from 8 to 12 times, in a weight ratio, the quantity of water contained in the mixture supplied as shown by numeral 5 in FIG. 1.

When the mixture supplied as shown by numeral 5 in FIG. 1 contains a considerable amount of water, and a very purified cyclic formal is desired to obtain, a considerable amount of n-pentane is needed. Accordingly, in the practice of the present invention, it is preferred that the mixture to be supplied be properly dehydrated in advance by ordinary distillation procedures or the like so as to raise the concentration of cyclic formal not less than 80% by weight to such a concentration close to an azeotrope. By this dehydrating operation, amounts of n-pentane to supply can be reduced, providing an economical and excellent purification process.

In the purification process according to the present invention, no particular limitation is imposed on the position at which the mixture containing a cyclic formal and water is supplied and the position at which n-pentane is supplied. If the supply position of the mixture is in a lower part of the tower, there are increased chances in which water and/or n-pentane migrate into the bottom liquid which is a purified cyclic formal. By contrast, if the mixture is supplied to the distillation tower at a high position, amounts of cyclic formal distilled off from the top will be increased. Accordingly, the position of supplying the mixture is preferably in the middle part of the distillation tower, avoiding lower ¼ and upper ¼ of the tower. The mixture to be supplied may be in the state of liquid or gas. Concerning the supply position of n-pentane, it is preferably between the top of the tower and the position at which the mixture is supplied, and in particular, the top of the tower is especially preferred.

No particular limitation is imposed on the types of distillation tower useful for purifying cyclic formals according to the present invention. In cases where plate distillation towers are used, any known types are usable including bubble cap tray, sieve tray, uniflux tray, bulb tray, Natter bulb tray, ballast tray, Venturi tray, Kittel tray, turbo grid tray, ripple tray and the like.

The distillation tower may be a packed distillation tower. Any types of packing materials are usable including those of ring types such as Raschig rings, Lessing rings, divided rings and pole rings; saddle types such as bar saddles and interlock saddles; and other types such as Goodroigh packings, Stedman packings, Dickson rings, McMahon packings, helix packings, teralet, cross-spiral packings and so on.

According to the purification process of the present invention, even when the mixture of cyclic formal and water to be supplied to the distillation tower contain unreacted formaldehyde or reaction byproducts, most of them can be satisfactorily removed. Moreover, although the cyclic formal obtained as a bottom liquid according to the present invention has been highly purified, it may further be subjected to another distillation or adsorption steps if extreme purification is necessary. The purification process of the present invention is particularly useful for purifying 1,3-dioxolan.

EXAMPLES

The present invention will further be described by way of examples, which however, should not be construed as limiting the invention thereto.

Example 1

Figure 2:
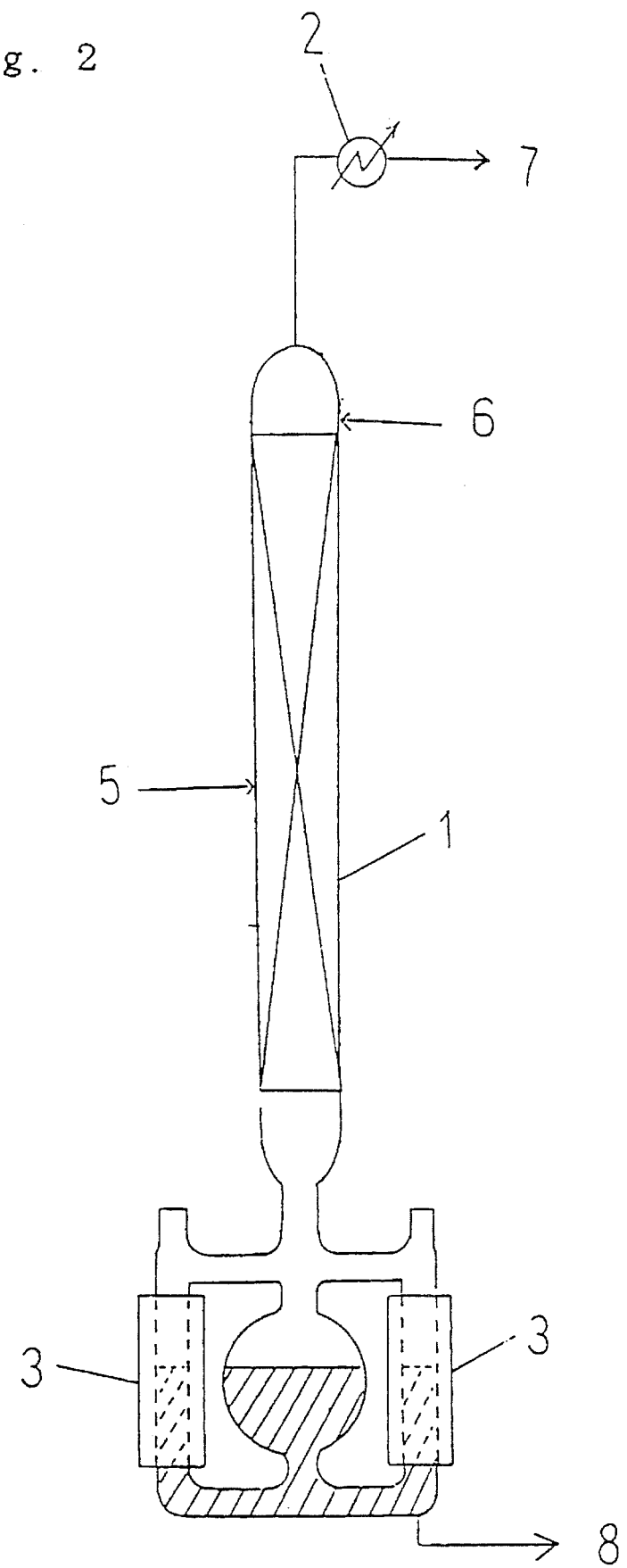
FIG. 2 is a schematic diagram showing the distillation system used in Example 1 according to the present invention and in Comparative Example 1.

Distillation was performed using a distillation tower (diameter of the tower=50 mm, 45 plates, sieve tray) as shown in FIG. 2, while feeding a mixture containing 93% by weight of 1,3-dioxolan and 7% by weight of water at the 35th plate counted from the bottom of the tower at a flow rate of 290 g/hr, and simultaneously feeding n-pentane at the top of the tower (=45th plate counted from the bottom) at a flow rate of 3671 g/hr. The compositions of the top distillate and the bottom liquid under steady conditions (the flow rate of the top distillate=4453 g/hr; the flow rate of the bottom liquid=260 g/hr) were as follows:

Top distillate: 1,3-Dioxolan (17.4% by weight),

Water (0.5% by weight), n-Pentane (82.1% by weight);

Bottom liquid: 1,3-Dioxolan (not less than 99.9% by weight),

Water (not more than 50 ppm), n-Pentane (not more than 50 ppm).

As apparent from the above, a very pure 1,3-dioxolan containing extremely small amounts of water and n-pentane was obtained as a bottom liquid.

Here, the mixture fed to the tower for purification had a composition very close to the azeotrope of 1,3-dioxolan and water, from which ordinary distillation procedures where n-pentane is not utilized cannot remove water any more, in other words, 1,3-dioxolan can no more be purified by conventional processes.

Comparative Example 1

The process of Example 1 was repeated except that cyclohexane is used in place of n-pentane, but stable operation was difficult to be continued. The reason is speculated that the boiling point of the top distillate containing cyclohexane, water and 1,3-dioxolan is relatively high and therefore a sufficient temperature difference between the top of the tower and bottom of the tower cannot be secured.

Example 2

Figure 3:
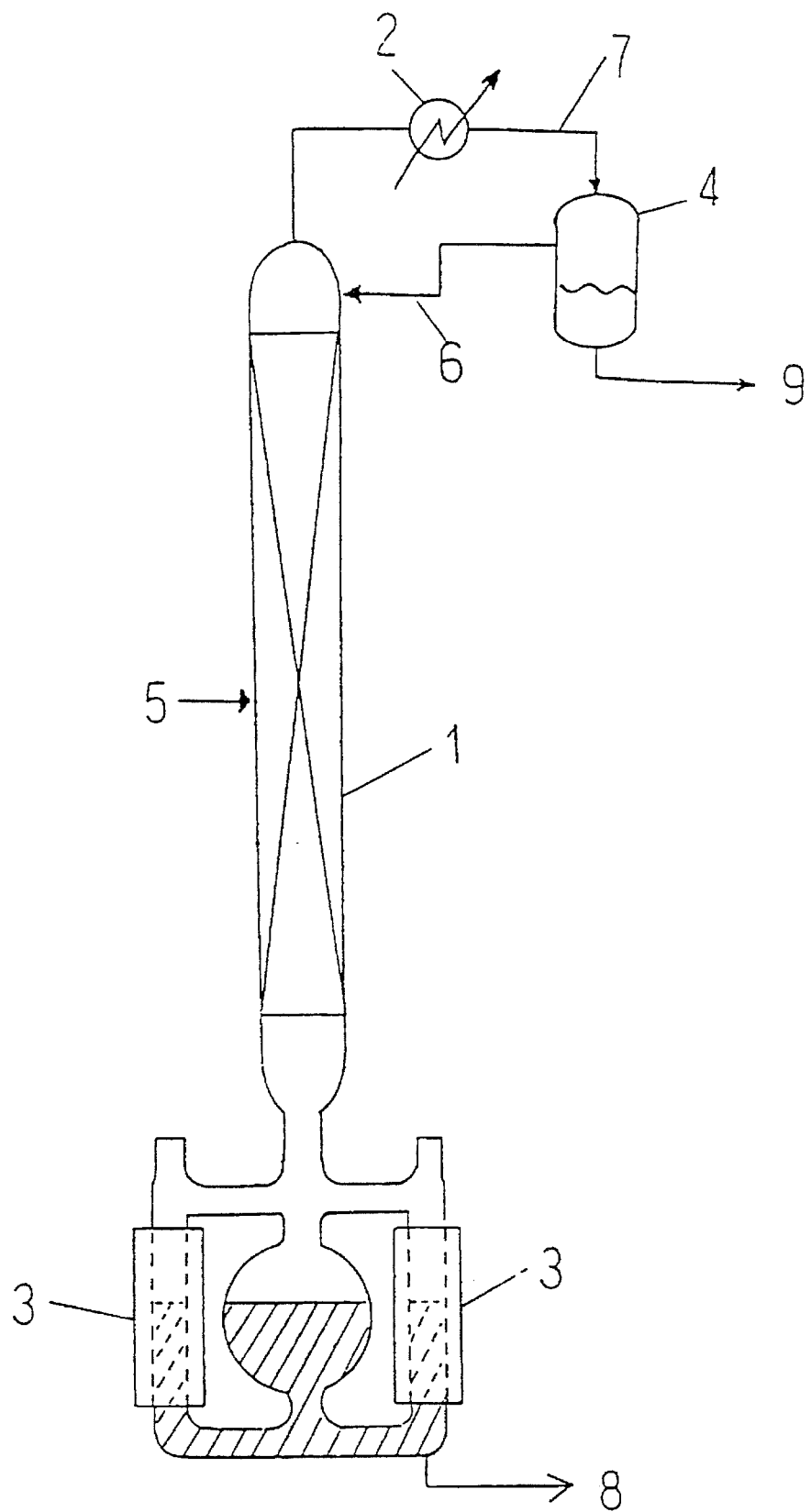
FIG. 3 is a schematic diagram showing the distillation system used in Example 2 according to the present invention.

Distillation was performed using a distillation tower (diameter of the tower=50 mm, 45 plates, sieve tray) as shown in FIG. 3. The process of Example 1 was followed except that the top distillate was cooled and allowed to separate into a n-pentane phase and an aqueous phase, and the obtained n-pentane phase was returned to the distillation tower. The flow rates and compositions of respective liquids under steady conditions are shown in Table 1.

TABLE 1

|  | Supplied mixture | n-Pentane phase | Top distillate | Bottom liquid |
|---|---|---|---|---|
| Flow rate (g/hr) | 290 | 4423 | 4453 | 260 |
| Composition |  |  |  |  |
| 1,3-Dioxolan | 93.00 | 16.90 | 17.02 | 99.92 |
| Water | 7.00 | 0.10 | 0.54 | (not more than 10) |
| n-Pentane | 0.00 | 83.00 | 82.44 | (not more than 10) |

Note: The values given under "Composition" are indicated by % by weight, with the exception that those in parentheses are indicated by ppm.

As described hereinabove, the present invention provides an economical purification process for crude cyclic formals containing water which was conventionally thought to be difficult to purify because of the azeotropy between the formals and water. The process of the invention yields highly pure cyclic formals on a steady basis, and is very useful and advantageous in the industry.

I claim:

1. A purification process for cyclic formals, comprising the steps of supplying a mixture of cyclic formals and water into a distillation tower; forming an azeotrope of cyclic formals and water; simultaneously supplying n-pentane into the tower at a position above the cyclic formals and water, wherein the azeotrope is destroyed while effecting distillation of the mixture; and taking out a purified cyclic formal as a bottom liquid from the tower, wherein the bottom liquid is characterized as exhibiting a concentration of about 99.9 weight percent cyclic formals and not more than 50 ppm of water.

2. The process according to claim 1, wherein the cyclic formals are selected from the group consisting of 1,3-dioxolan, 1,4-butanediol formal, diethylene glycol formal and methyl-1,3-dioxolan.

3. The process according to claim 2, wherein the mixture supplied to the tower comprises at least about 80 weight percent of cyclic formals.

4. The process according to claim 3, wherein the quantity of n-pentane supplied to the tower is from 5 to 20 times the quantity of water in the mixture, based on the weight of the mixture.

5. The process according to claim 4, wherein the cyclic formal is 1,3-dioxolan.

* * * * *